United States Patent
Rönnberg

[11] Patent Number: 5,556,393
[45] Date of Patent: Sep. 17, 1996

[54] INSERT FOR AN ABSORBENT ARTICLE

[75] Inventor: Peter Rönnberg, Mölndal, Sweden

[73] Assignee: Molnlycke AB, Gothenburg, Sweden

[21] Appl. No.: 107,706

[22] PCT Filed: Feb. 28, 1992

[86] PCT No.: PCT/SE92/00124

§ 371 Date: Aug. 19, 1993

§ 102(e) Date: Aug. 19, 1993

[87] PCT Pub. No.: WO92/15269

PCT Pub. Date: Sep. 17, 1992

[30]     Foreign Application Priority Data

Mar. 1, 1991 [SE] Sweden ................... 9100593

[51] Int. Cl.$^6$ .................................. A61F 13/15
[52] U.S. Cl. .............. 604/385.2; 604/369; 604/374
[58] Field of Search ................... 128/98.1, 889;
602/67–73; 604/327, 346, 347, 349, 355,
356, 366, 369, 381–387, 394–396, 374

[56]           References Cited

U.S. PATENT DOCUMENTS

| 3,654,929 | 4/1972 | Nilsson et al. | 604/378 |
| 3,717,150 | 2/1973 | Schwartz | 604/383 |
| 3,882,871 | 5/1975 | Taniguchi | 604/391 |
| 3,886,941 | 6/1975 | Duane et al. | 604/366 |
| 3,927,673 | 12/1975 | Taylor | 604/366 |
| 4,360,021 | 11/1982 | Stima | 604/369 |
| 4,389,211 | 6/1983 | Lenoghan | 604/383 |
| 4,692,163 | 9/1987 | Widlund | 604/385.2 |
| 4,772,281 | 9/1988 | Armstead | 604/376 |
| 4,938,756 | 7/1990 | Salek | 604/378 |
| 5,129,893 | 7/1992 | Thoren | 604/385.2 |
| 5,217,447 | 6/1993 | Gagnon | 604/391 |
| 5,246,431 | 9/1993 | Minetola et al. | 604/385.1 |

FOREIGN PATENT DOCUMENTS

| 0167931 | 1/1986 | European Pat. Off. . | |
| 8903868 | 11/1989 | Sweden . | |
| 666612 | 8/1988 | Switzerland . | |
| WO86/05386 | 9/1986 | WIPO . | |
| 8707136 | 12/1987 | WIPO | 604/349 |
| 9107155 | 5/1991 | WIPO | 604/349 |

*Primary Examiner*—David H. Willse
*Assistant Examiner*—K. M. Reichle
*Attorney, Agent, or Firm*—Young & Thompson

[57]            ABSTRACT

An insert intended to be worn by a male incontinent and which, in use, is worn around the wearer's genitals, within an absorbent article, such as a diaper or an incontinence guard. The insert has a basin-like configuration and includes at least one opening (12) which enables liquid to flow through the insert, and elastic devices (4, 5) are disposed in the edge parts (6, 7) of the insert, such that, in use, the insert will retain its basin-like configuration and be held securely around the wearer's genitals.

10 Claims, 2 Drawing Sheets

INSERT FOR AN ABSORBENT ARTICLE

FIELD OF THE INVENTION

The present invention relates to an insert which is intended to be carried by a male user and to be placed, in use, around the genitals of the wearer, within an absorbent article, such as a diaper or an incontinence guard. When designing incontinence guards for adult persons, it is necessary to bear in mind that the degree of incontinence, and therewith the volume of body fluid discharged, can vary greatly from person to person. Furthermore, the requisite absorbency of an article, may vary for one and the same individual. For example, the article is often required to absorb a greater amount of body fluid during the night, since the incontinence guard is not changed as often as it is during the day. In order to meet these different absorbency requirements, it is therefore necessary to manufacture adult incontinence guards in various sizes. A large range of sizes, however, results in higher manufacturing costs and storage costs. Consequently, it is desirable to limit the number of sizes to the greatest possible extent.

Incontinence guards are also required to be narrow, discrete when worn and highly reliable against leakage. Since the size of the incontinence guard is directly contingent on its absorbency, the guard should be constructed in a manner which will enable the available absorbent material to be utilized to the full. This creates a particular problem in the case of male incontinence guards, since the male anatomy makes it difficult to know precisely where the liquid discharged will impinge on the guard. This is because the wearer's penis is able to move within the guard as the wearer moves, for instance. It is also possible to position the guard wrongly, such that the penis is initially located in an inappropriate position, for instance pointed up towards the wearer's stomach or towards one edge of the guard. Such wrong positioning of the incontinence guard may be because the incontinent is handicapped and is unable to use his hands properly, which is quite usual with older males. Another reason may be because the person fitting the guard is unfamiliar with how the guard should be positioned or is in too much of a hurry.

Randomly chosen parts of the absorbent material will be utilized in the absorption of liquid, depending on the position of the penis within the incontinence guard. In this regard, there is a serious risk that one edge part of the guard will become saturated with liquid and that when further liquid is discharged this liquid will be displaced and leak from the guard, despite the fact that parts of the absorbent material have not been used in absorbing or taking up liquid. There is a particular risk of urine splashing and leaking from the guard, when the wearer's penis is directed vertically towards the stomach of the wearer. This is primarily a problem when the incontinent lies on his back. Since many male incontinents under hospital care are bed-ridden, the care of these patients would be greatly facilitated if the problems associated with urine leakage were solved, so as to reduce the number of times which bed linen and clothes need to be changed. Older men often have a small and retarded penis and therewith present a particular problem, since they are unable to use urine-collecting tubes, bottles or like devices which are intended to be fitted over the penis. The need for a well-functioning incontinence guard is particularly great in the case of male incontinents who suffer this particular affliction.

The majority of incontinence guards used at present by male incontinents are primarily constructed to suit female incontinents. This is not because no incontinence guards that have been designed particularly for males are available, but primarily because the majority of adult incontinents are women. The use of female incontinence guards thus affords satisfactory reliability against leakage for the majority of users. At the same time, the number of different variations of incontinence guards can be kept low, which is a cost advantage, as before mentioned.

Since female wearers normally wet the incontinence guard within a relatively well-defined area around the mouth of the urethra, it is relatively simple to optimize absorbency and reduce the risk of leakage with incontinence guards that are intended for female wearers. Thus, a female incontinence guard has a relatively high absorbency within the region where wetting is most likely to occur, whereas remaining parts of the guard have a lower absorbency. When an incontinence guard of this kind is used by male incontinents, the risk of leakage is, of course, high, since it is impossible to control the location or point on the guard which will receive the initial urine discharge. It has been necessary to take a number of more or less satisfactory measures in order to reduce the risk of leakage. For instance, it is not unusual for male incontinents to use two incontinence guards at the same time, wherein the one guard is wrapped around the penis and scrotum and the other guard is placed conventionally outside the wrapping. Although this solution may be effective from the aspect of leakage, it does not, however, fulfil the discretion requirement, since the large, bulgy wrapping is impossible to hide beneath conventional clothing. Neither is it unusual for male incontinents to use an incontinence guard which has greater absorbency than that which is actually necessary with sole regard to the amount of liquid discharged.

EP 140 478 describes an incontinence guard in the form of a liquid-impervious bag filled with absorbent material. The bag is provided with an opening through which body fluid can pass into the absorbent material. In the case of one embodiment intended for male incontinents, a pocket is provided adjacent the bag opening. When this guard is worn, the wearer's penis is inserted down into the pocket, so that discharged urine will be guided through the opening and can be absorbed within the bag. Although the flow of liquid into this incontinence guard is controlled to some extent, the guard is nevertheless encumbered with a number of disadvantages. For example, an incontinence guard constructed in accordance with EP 140 478 is particularly uncomfortable to wear, since the wearer's penis is held firmly in the guard during use. When the wearer walks, or moves in some other way, the guard will also move rhythmically with the wearer's movements, which naturally feels uncomfortable and which, furthermore, can cause the wearer's penis to slide from the pocket in the guard. This problem becomes progressively more pronounced with increasing sizes of incontinence guards. In the case of large incontinence guards intended for people who are unable to control all evacuative functions, i.e. both urine and faecal incontinence, the arrangement of a pocket in accordance with EP 140 478 does not provide an appropriate solution. This known incontinence guard is, however, intended for people who suffer solely urine incontinence and can therefore be made relatively small. A further drawback with these known incontinence guards is that they must be constructed in a number of different sizes of mutually different absorbencies, in order to suit incontinents of differing degrees of incontinence.

SE 8903869-9 teaches an absorbent insert which is intended to be used inside a diaper or an incontinence guard. The insert is comprised of an absorbent body or pad which is enclosed between two casing layers of mutually different liquid permeability. In this case, the inner casing layer, which is intended to face the wearer in use, has a greater liquid permeability than the outer casing layer, which is intended to face towards the diaper or incontinence guard in use. The underlying concept of this insert is that body fluid which is absorbed by the insert shall pass through the outer casing layer of the insert in a slow and controlled fashion and be collected in the diaper or incontinence guard. It has been found, however, that the transfer of fluid from the insert to the diaper or incontinence guard is much too slow and that, as a result, when urine is discharged the insert may become filled with liquid which will flow out beyond the edges of the insert and give rise to leakage. Furthermore, because of the slow transfer of liquid from the insert into the diaper or incontinence guard, the insert will remain wet for a long period of time after each urine discharge. Since, when worn, the insert is intended to lie over the wearer's genitals, in direct contact with the wearer's skin, a wet insert is particularly uncomfortable to carry and can cause irritation of the skin.

SUMMARY OF THE INVENTION

The present invention, however, provides an incontinence guard for male incontinents which removes the drawbacks of earlier known incontinence guards and incontinence inserts. An insert constructed in accordance with the invention is primarily characterized in that it has a cup or basin-like configuration and is provided with at least one opening which enables liquid to flow through the insert, and in that elastic devices are provided around the edge parts of the insert, thereby maintaining the basin-like configuration of the insert in use and holding the insert around the wearer's genitals.

According to one embodiment of the invention, the insert includes a first casing layer, a second casing layer, and a body or pad which is enclosed between said first and second casing layers and which is comprised essentially of a porous, flexible material, such as fibre wadding which includes hydrophilic or hydrophobic fibres or mixtures thereof.

According to other embodiments of the invention, the porous, flexible material is cellulose fluff or plastic foam.

According to another embodiment of the invention, the insert is provided with a plurality of openings in the form of penetrating holes or slots which are formed through the two casing layers within a region of the insert which is free from porous, flexible material, and the porous, flexible material substantially surrounds the perforated region of the insert.

According to a further embodiment of the invention, the insert is formed from a blank which has a generally flat, triangular shape, and in which pre-stretched elastic devices in the form of elastic bands of threads are disposed along at least two of the side edges of the blank, whereby the insert is given a basin-like configuration which presents a curved narrowing part which, in use, is intended to embrace the wearer's scrotum, either completely or partially, and a broader part which, in use, is intended to lie over the wearer's penis.

According to another embodiment of the invention, the insert is formed from a blank of generally rectangular shape, and prestretched or pretensioned elastic devices in the form of elastic bands or threads are disposed along at least two mutually parallel edges of the blank, whereby the insert is given a basin-like, curved configuration. In another embodiment of the invention, at least one of the casing layers is comprised of a material which is completely or partially liquid-impermeable.

Because the inventive insert has a basin-like configuration, so that the insert will at least partially surround the wearer's penis and scrotum in use, the body fluid discharged can be collected effectively. The body fluid which collects in the insert is able to pass quickly through the perforated part of the insert and be absorbed by the incontinence guard located outside the insert. The flow of fluid to desired locations in the incontinence guard can be controlled by appropriate selection of the position of the perforated region in the insert. An inventive insert can thereby be advantageously used for adapting a female incontinence guard so that it can also be used by male incontinents without risk of leakage.

An inventive insert is also small and easy to handle, and will suit all male incontinents irrespective of their degree of incontinence. The insert can also be used together with incontinence guards of different sizes. Thus, a single type of insert can be used throughout the whole of the available range of incontinence guards intended for female incontinents. This provides a simple and inexpensive method of providing well-functioning, individually-adapted incontinence guards for men, without the necessity of providing different ranges or assortments of male and female incontinence guards.

In addition to considerably reducing the risk of urine splashes and urine leakage, an inventive insert is also more comfortable to the wearer, since it is possible to choose a smaller, more discrete incontinence guard. The inventive insert also avoids the necessity of using large, clumsy diaper wrappings and other less suitable solutions.

Furthermore, the discharged body fluid passes quickly through the insert and into the incontinence guard, therewith leaving the insert dry and comfortable to the wearer.

Moreover, an incontinence guard can be more readily positioned externally of the insert, since no particular care need be taken to ensure that the wearer's penis is positioned correctly within the guard. This is, of course, highly beneficial to nursing personnel who are required to change the incontinence guards worn by heavy, handicapped patients, besides being beneficial to incontinents who change their own incontinence guards.

It is important to the invention that the holes in the perforated part of the insert are not so large that the wearer's genitals will protrude through the insert during use. It is also essential that the edge parts of the insert are sufficiently elastic to be held firmly around the wearer's genitals in use.

BRIEF DESCRIPTION OF THE DRAWINGS

The invention will now be described in more detail with reference to exemplifying embodiments thereof illustrated in the accompanying drawings.

DETAILED DESCRIPTION OF THE INVENTION

Figure 1:
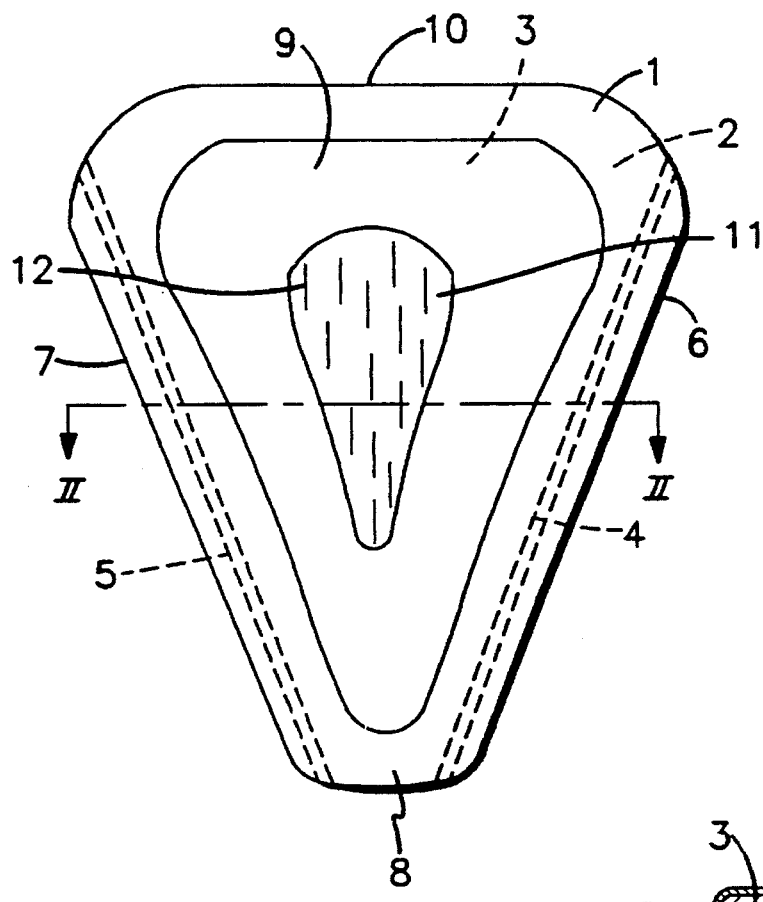
FIG. 1 of the accompanying drawings illustrates an insert according to a first embodiment of the invention in a flat state and seen from the side of the insert which faces the wearer in use.
Figure 2:
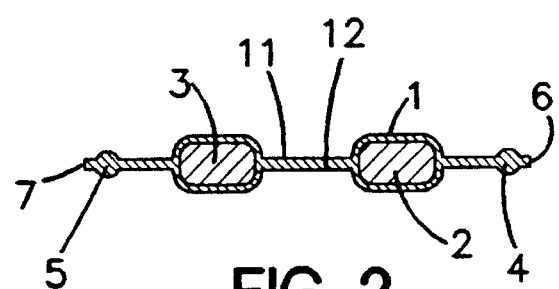
FIG. 2 is a sectional view of the insert shown in FIG. 1, taken on the line II—II in said Figure.
Figure 3:
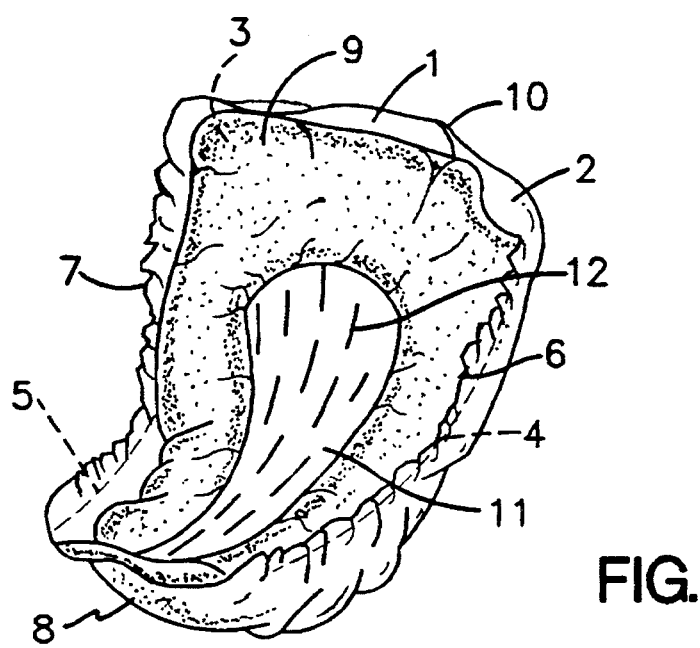
FIG. 3 is a perspective view of the insert shown in FIG. 1 in a relaxed or contracted state.

The insert illustrated in FIGS. 1–3 comprises a first, inner casing layer 1 which is intended to face towards the wearer in use, a second, outer casing layer 2, which is intended to face away from the wearer in use, and an absorbent pad 3 which is enclosed between the two casing layers 1, 2. The casing layers 1, 2 may be formed from the same or different material and may, for instance, be comprised of liquid-permeable, non-woven fabric or of a perforated plastic film. It is therewith appropriate to choose a material which is relatively hydrophobic and which has little or no liquid absorbency, particularly in the case of the inner casing layer 1, since the surface nearest the wearer's skin will therewith remain essentially dry during use. The outer casing layer 2 may be liquid-impermeable, although it will preferably be permeable to air and water vapour, with regard to the wearer's comfort. The inner casing layer 1 may also be partially liquid-impermeable, for instance along the edges of the layer. The absorbent pad 3 may consist of cellulose fluff or some other hydrophilic fibre material for instance, either with or without an admixture of some form of so-called superabsorbent material, i.e. polymeric material which can absorb several times its own weight of water or body fluid. Superabsorbents are found in several physical forms, such as in the form of flakes, fibres, powder and granules. The absorbent pad 3 may also be comprised of a hydrophilic foam material. Since the insert shown in FIGS. 1–3 is primarily intended to capture body fluid and to pass this fluid to the outwardly-lying absorbent incontinence guard, the absorbent pad 3 need only have an absorbency sufficient to absorb small quantities of liquid. It is therefore possible to use material of relatively low absorbency in this case.

As will best be seen from FIG. 1, when in a stretched state, the inventive insert has the form of an isosceles triangle with rounded corners. Elastic threads 4, 5 are applied in a stretched state along the two mutually opposing edges 6, 7 of equal lengths along the insert. When the tension in the threads is relaxed, the threads will contract and therewith impart to the insert a curved, basin-like or cup-like configuration, with the corner part 8 between said two mutually opposing long edges 6, 7 being curved upwards in a direction towards the inner casing layer 1. In use, the upwardly curved corner part 8 is intended to be located rearwardly on the wearer and therewith to surround the wearer's scrotum, either completely or partially, whereas the broader region 9 around the edge 10 opposite the corner 8 is intended to be located forwardly on the wearer and lie over the wearer's penis. Because of the particular configuration of the insert and also because of the tension in the elastic devices 4, 5, the insert is essentially prevented from being moved outwards and away from the wearer's body by the outwardly-lying incontinence guard in use, therewith positively retaining the insert around the wearer's genitals without needing to provide separate securing devices to this end.

The insert illustrated in FIGS. 1–3 also includes a liquid transfer region 11, which is free from absorbent material and which has a high degree of liquid permeability. The liquid transfer region 11 is comprised of a penetrating hole in the absorbent body 3, and has generally the same shape as said body, or pad. The two casing layers 1, 2 are mutually joined within the whole of the liquid transfer region 11 and are provided with a plurality of penetrating slits 12 which enable liquid to pass quickly through the liquid transfer region 11.

In use, discharged body fluid is collected by the insert and runs along the inner casing layer 1 to the liquid transfer region 11. The transfer or draining of fluid from the insert to the incontinence guard is particularly effective when the wearer stands or sits up, since the force of gravity then coacts with the basin-like configuration of the insert to transport body fluid to the liquid transfer region 11. The transfer of fluid from the insert to the outwardly-lying incontinence guard is somewhat slower when the wearer adopts a recumbent position, although the insert will effectively guide the liquid flow to a limited, well-defined area of the incontinence guard even in this case. The absorbent material around the periphery of the liquid transfer region 11 will absorb any liquid that may remain within the insert, therewith preventing splashing and leakage of urine beyond the edges of the insert. When the casing layers 1, 2 are permeable to liquid, that liquid which has collected in the absorbent pad 3 of the insert will gradually transfer to the incontinence guard lying externally of the insert.

Figure 4:
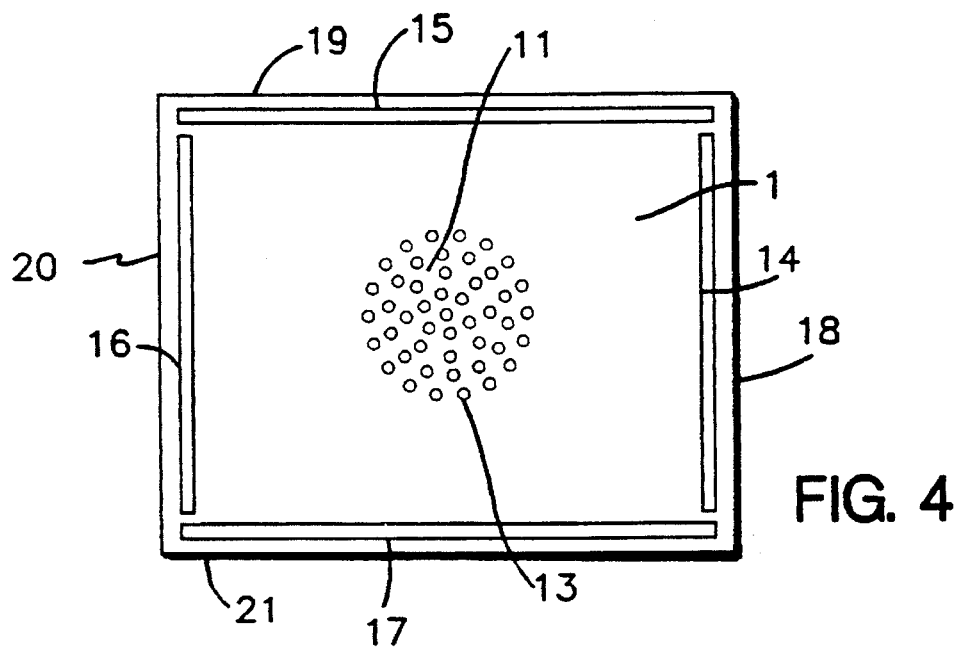
FIG. 4 illustrates an insert according to a second embodiment of the invention, the insert being shown in a stretched state and is seen from the side of the insert which faces towards the wearer in use.
Figure 5:
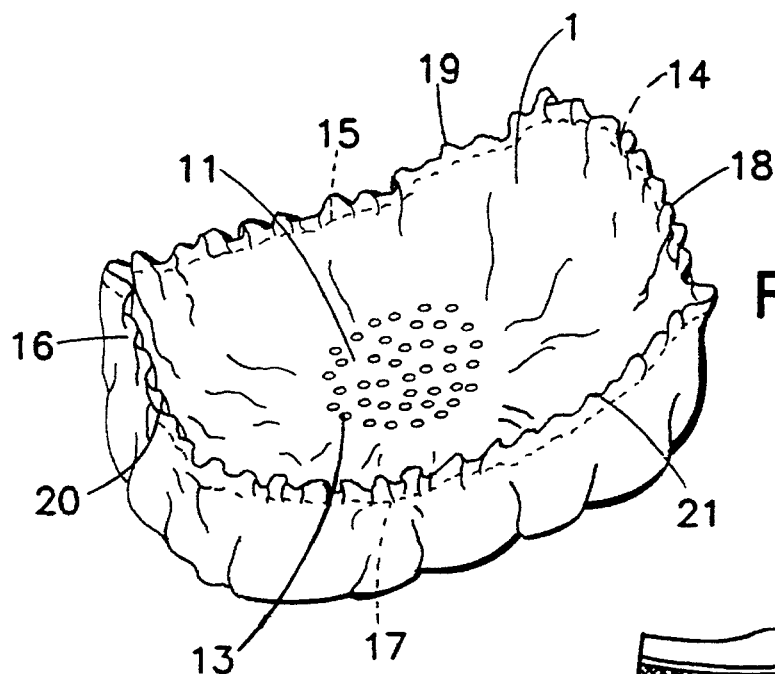
FIG. 5 is a perspective view of the insert shown in FIG. 4, in a relaxed or contracted state.

The insert illustrated in FIGS. 4 and 5 is comprised of a layer 1 which is made, for instance, of non-woven fabric, plastic fill or foam material. When in a stretched state, the insert has an essentially rectangular shape and includes a centrally located liquid-transfer region 11, within which a plurality of holes 13 are formed, through which liquid is able to leave the insert, through the liquid transfer region 11, practically unimpeded.

Elastic devices 14–17, for instance elastic threads or bands, are applied in a stretched state along the four edges 18–21 of the insert, so that when the tension in said devices is relaxed the devices will contract and impart to the insert will be given a curved, basin-like configuration, as shown in FIG. 5. When worn, the insert is intended to be positioned over the wearer's penis and scrotum, an essential criterion being, in this respect, that the pre-tension in the elastic devices 14–17 is such that the insert will be held in position without requiring the need for separate securing devices to this end.

Figure 6:
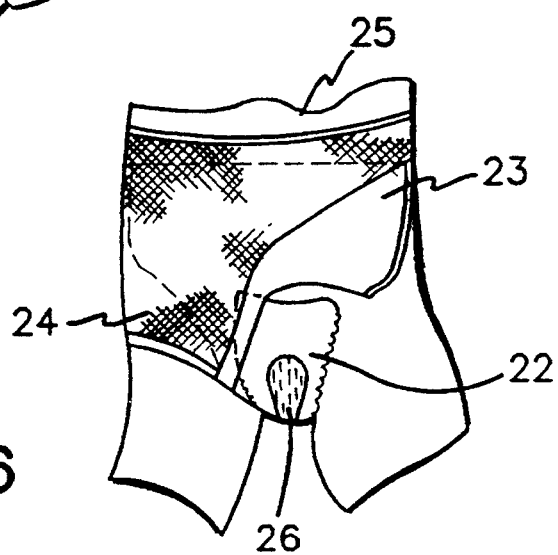
FIG. 6 is a perspective view of an inventive insert placed within an absorbent incontinence guard held in position by underpants, with parts of the guard and the underpants broken away.

The insert 22 illustrated in FIG. 6 is of the same kind as that illustrated in FIGS. 1–3. The insert 22 is shown in use inwardly of an incontinence guard 23 which is held in position by means of elastic underpants 24. For the sake of clarity, parts of the underpants 24 and the incontinence guard 23 have been omitted from the Figure. The insert 22 is placed in the crotch of a male wearer 25, indicated in the Figure, and lies over and surrounds the wearer's genitals.

In the event of a urine discharge, the body liquid is captured by the insert and is conducted to the incontinence guard 23 at its crotch part 26. The illustrated incontinence guard 23 is of a kind generally used and is primarily intended for female incontinents. The absorbency of such incontinence guards is often optimized for a liquid discharge which impinges on the incontinence guard 23 in precisely the crotch region 26. It will be understood, however, that it is possible to guide the liquid flow to some other particularly suitable region of an incontinence guard, by means of the inventive insert, by choosing an appropriate position for the liquid transfer region in said insert.

It will be understood that the invention is not restricted to the aforedescribed and illustrated embodiments. For example, the configuration and the position of the liquid transfer region in the insert may be different to that described and illustrated. Furthermore, the shape of the openings in the liquid transfer region and the number of openings provided may also be varied.

The material from which the insert is made may be either completely or partially liquid-impermeable, although, with regard to wearer's comfort, it should at least be permeable to air and moisture. The elastic devices may consist, for instance, of elastic bands of foam material, or covered rubber threads. The requisite elasticity can also be achieved with the use of elastic nonwoven fabrics, knitted or crocheted materials.

It is also appropriate to construct the insert so that it will have a given intrinsic absorbency, primarily to ensure the transportation of liquid to outwardly-lying absorbent articles. This is not a necessary feature of the invention, however. For example, the insert may be generally non-absorbent and given an upwardly raised edge of generally non-absorbent fibre wadding or foam material which functions to prevent liquid from splashing or running beyond the edge of the insert.

It will also be understood that the shape of the insert itself can be varied. For instance, the insert may be formed from a round or square material blank. It is also conceivable to engender the basin-like configuration of the insert in some other way than through the medium of the contractibility of elastic devices. For instance, the basin-like configuration can be achieved by hot-pressing or folding a material layer. It is essential, however, that the edges of the insert are imparted sufficient elasticity to ensure that the insert will be kept in position in use.

I claim:

1. An insert which is intended to be worn by a male incontinent and to be placed, in use, around the male incontinent's genitals, within an absorbent article, said insert having a basin-shaped configuration having a thickness and comprising edge parts, said insert further comprising a liquid transfer region having at least one perforation which penetrates through the whole thickness of the insert and which allows liquid to flow through the insert, elastic devices being disposed in said edge parts thereby retaining the basin-shaped configuration of the insert in use and holding the insert firmly around the male incontinent's genitals.

2. An insert according to claim 1, wherein said insert includes a first casing layer, a second casing layer, and a pad consisting essentially of a porous, flexible material enclosed between the casing layers.

3. An insert according to claim 2, wherein the porous, flexible material is fiber wadding which includes hydrophilic or hydrophobic fibers or a mixture of such fibers.

4. An insert according to claim 3, wherein the fiber wadding is comprised essentially of cellulose fluff.

5. An insert according to claim 3, wherein said insert includes a plurality of perforations in the form of penetrating holes or slots which are formed through the two casing layers within a region of the insert which is free from the porous, flexible material; and said porous, flexible material generally surrounding said region.

6. An insert according to claim 2, wherein the porous, flexible material is plastic foam.

7. An insert according to claim 2, wherein at least one of the casing layers is comprised of a material which is completely or partially impermeable to liquid.

8. An insert according to claim 1, wherein the insert is formed from a blank having a generally flat, triangular shape with side edges; and the elastic devices are in the form of elastic bands or threads disposed along at least two of the side edges of said blank, thereby to form said basin-shaped configuration which includes a curved, narrowing part which is intended, in use, to surround the male incontinent's scrotum, either completely or partially, and a broader part which, in use, is intended to lie over the male incontinent's penis.

9. An insert according to claim 1, wherein the insert is formed from a blank of generally rectangular shape; and the elastic devices are in the form of elastic bands or threads disposed along at least two mutually parallel edges of the blank, thereby to provide said basin-shaped configuration.

10. An insert which is intended to be worn by a male incontinent and to be placed, in use, around the male incontinent's genitals, within an absorbent article, said insert having a basin-shaped configuration having a thickness and comprising edge parts surrounding a liquid transfer region having at least one perforation which penetrates through the whole thickness of the insert for allowing liquid to flow through the insert, said insert transfer region having a higher permeability to liquid than the edge parts surrounding the transfer region, elastic devices being disposed in said edge parts thereby retaining the basin-shaped configuration of the insert in use and holding the insert firmly around the male incontinent's genitals.

* * * * *